(12) United States Patent
Woodward et al.

(10) Patent No.: US 7,868,032 B2
(45) Date of Patent: Jan. 11, 2011

(54) PROSTAMIDE RECEPTOR ANTAGONISTS

(75) Inventors: David F. Woodward, Lake Forest, CA (US); Jenny W. Wang, Newport Coast, CA (US); Clive L. Cornell, Saffron Walden (GB); Hans G. Fliri, Saffron Walden (GB); Jose L. Martos, Basildon (GB); Simon N. Pettit, Colchester (GB)

(73) Assignee: Allergan, Inc., Irvine, CA (US)

( * ) Notice: Subject to any disclaimer, the term of this patent is extended or adjusted under 35 U.S.C. 154(b) by 732 days.

(21) Appl. No.: 11/869,697

(22) Filed: Oct. 9, 2007

(65) Prior Publication Data

US 2008/0096240 A1    Apr. 24, 2008

Related U.S. Application Data

(60) Provisional application No. 60/829,919, filed on Oct. 18, 2006.

(51) Int. Cl.
  *A61K 31/422*  (2006.01)
  *C07D 263/30*  (2006.01)
  *C07D 311/02*  (2006.01)

(52) U.S. Cl. .................. 514/374; 548/236; 549/398

(58) Field of Classification Search .............. 514/374; 548/236; 549/398
See application file for complete search history.

(56) References Cited

U.S. PATENT DOCUMENTS 5,153,327 A * 10/1992 Misra et al. .................. 548/237

* cited by examiner

*Primary Examiner*—Kamal A Saeed
*Assistant Examiner*—Samantha L Shterengarts
(74) *Attorney, Agent, or Firm*—Kevin J. Forrestal; John E. Wurst; Doina G. Ene

(57) ABSTRACT

The present invention provides prostamide receptor antagonist compounds that may be represented by the general formula I

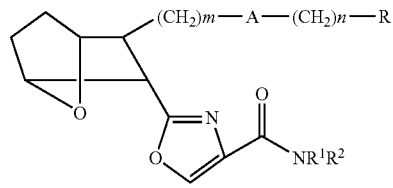

wherein A, $R^1$, $R^2$, $R^3$, $R^4$ and $R^6$ are as defined in the specification.

27 Claims, No Drawings

PROSTAMIDE RECEPTOR ANTAGONISTS

RELATED APPLICATION

This application claims the benefit of U.S. Provisional Application Ser. No. 60/829,919, filed Oct. 18, 2006, which is hereby incorporated by reference in its entirety.

BACKGROUND OF THE INVENTION

1. Field of the Invention

The present invention provides prostamide receptor antagonists, e.g. prostamide $F_{2\alpha}$ receptor antagonists.

2. Description of Related Art

Prostamides are disclosed in U.S. Pat. No. 6,395,787, hereby incorporated by reference in its entirety, as useful to lower elevated intraocular pressure and for treating glaucoma. These compounds are structurally related to prostaglandins, e.g. Prostaglandin $F_{2\alpha}$, which are also useful in lowering elevated intraocular pressure, but prostamides do not act through the FP receptor to lower intraocular pressure. As such, prostamides do not have the same effects as prostaglandins when utilized to treat elevated intraocular pressure and/or glaucoma. For example, it has been demonstrated that bimatoprost, a synthetic analog of prostamide $F_{2\alpha}$, lowers intraocular pressure in patients unresponsive to the synthetic prostaglandin $F_{2\alpha}$ analog latanoprost (Gandolfi and Cimino, Opthalmology 110:609, 2003).

It would be desirable to have prostamide receptor antagonists to assist in pharmacologically defining prostamide receptors to aid in determining compounds which have activity at the prostamide receptor. Compounds having prostamide receptor antagonist activity have been reported in U.S. Pat. No. 7,045,634.

Prostaglandin $F_{2\alpha}$ antagonists are reported in U.S. Pat. Nos. 4,632,928; 5,747,660; and 5,955,575. The $PGF_{2\alpha}$ antagonists of U.S. Pat. No. 4,632,928 are pyrazole derivatives having an ergoline skeleton. The $PGF_{2\alpha}$ antagonist of U.S. Pat. No. 5,747,660 is a prostaglandin $F_{2\alpha}$ receptor regulatory protein (FPRP) which is able to inhibit the binding of $PGF_{2\alpha}$ to its receptor.

Novel prostaglandin F2α antagonists are reported in U.S. Pat. Nos. 6,369,089; 6,407,250; 6,509,364 and 6,511,999 which are hereby incorporated by reference in their entirety.

Interphenylene 7-Oxabicyclo[2.2.1]heptane oxazoles, useful as Thromboxane $A_2$ receptor antagonists are reported in U.S. Pat. Nos. 5,100,889 and 5,153,327, European Patent Application 0 391 652 and J. Med. Chem. 1993, 36, 1401-1417.

Thromboxane $A_2$ receptor antagonists, e.g. 7-oxabicycloheptyl substituted heterocyclic amide prostaglandin analogs, alone, or in combination with anti-inflammatory agents are useful in treating ulcerative gastrointestinal conditions and dysmenorrhea as disclosed in European Patent Application 0 448 274 and U.S. Pat. No. 5,605,917.

BRIEF SUMMARY OF THE INVENTION

The invention relates to prostamide receptor antagonists, e.g. prostamide $F_{2\alpha}$ receptor antagonists and their use in determining compounds having activity at the prostamide receptor, i.e. prostamide receptor agonists.

The compounds useful as prostamide receptor antagonists of the present invention may be represented by the general formula I.

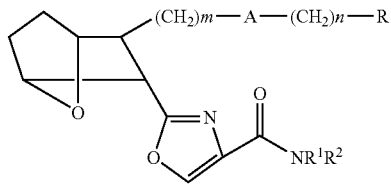

wherein m is an integer of from 1 to 3, preferably 1 or 2;
n is 0 or an integer of from 1 to 4, preferably from 2 to 4;
A is an aryl or heteroaryl radical having from 6 to 14 carbon atoms, wherein said heteroaryl may be substituted with one or more oxygen, sulfur or nitrogen in the heteroaryl ring and heteroatom substituted derivatives thereof;
R is $OCH_2CONR^3R^4$;
$R^1$ and $R^2$ are independently selected from the group consisting of H, $C_1$-$C_6$ alkyl, $C_2$-$C_6$ alkenyl, $C_2$-$C_6$ alkynyl, $C_3$-$C_7$ cycloalkyl, $C_4$-$C_{12}$ alkylcycloalkyl, $C_6$-$C_{10}$ aryl, $C_7$-$C_{12}$ alkylaryl radicals and heteroatom-substituted derivatives thereof, wherein one or more of the hydrogen or carbon atoms in said radicals may be replaced with a halogen, oxygen, nitrogen or sulfur-containing radical;
$R^3$ and $R^4$ are independently selected from the group consisting of H, $C_1$-$C_6$ alkyl, $C_2$-$C_6$ alkenyl, $C_2$-$C_6$ alkynyl, $C_3$-$C_7$ cycloalkyl, $C_4$-$C_{12}$ alkylcycloalkyl, $C_6$-$C_{10}$ aryl, $C_7$-$C_{12}$ alkylaryl radicals and heteroatom-substituted derivatives thereof, wherein one or more of the hydrogen or carbon atoms in said radicals may be replaced with a halogen, oxygen, nitrogen or sulfur-containing radical; and pharmaceutically acceptable salts thereof.

The preferred substituents for $R^1$, $R^2$, $R^3$ and $R^4$ are selected from the group consisting of hydroxyl, halogen, e.g. fluoro or chloro, $COOR^6$, $NO_2$, $N(R^6)_2$, $SR^6$, sulfoxy, sulfone, CN and $OR^6$.

These compounds are especially useful for determining compounds having prostamide agonist activity, e.g. prostamide $F_{2\alpha}$ activity, as well as for treating a number of diseases. For instance, prostamide antagonists may be useful in treating hyperpigmentary disorders of the skin, hair, internal organs or other pigmented cells. Additionally, prostamide antagonists may be useful in reducing hair growth, e.g. in case of hirsutism or in instances where a reduction or prevention of hair growth may be desirable. Also, prostamide antagonists may be useful in treating ocular hypotony associated with disease or surgery. Finally, prostamide antagonists may be useful in treating inflammatory and auto-immune diseases such as, but not limited to, reheumatoid arthritis, uveitis, and conjunctivitis.

DETAILED DESCRIPTION OF THE INVENTION

In the prostamide receptor antagonists of the present invention, A may be represented by the general formula

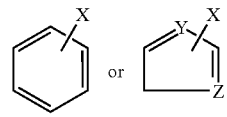

wherein X is selected from the group consisting of H, $R^6$, hydroxy, halogen, e.g. fluoro or chloro, $COOR^6$, $NO_2$, $CF_3$, $N(R^6)_2$, $CON(R^6)_2$, $SR^6$, sulfoxy, sulfone, CN and $OR^6$ wherein $R^6$ is $C_1$-$C_6$ alkyl;

Y is O or S; Z is N or CH

Preferably, the prostamide antagonist compounds are represented by the general formula II.

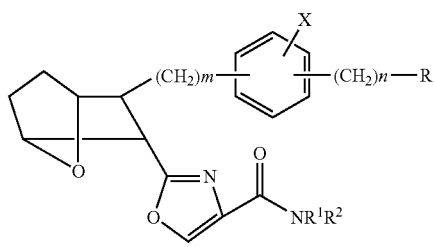

or general formula III

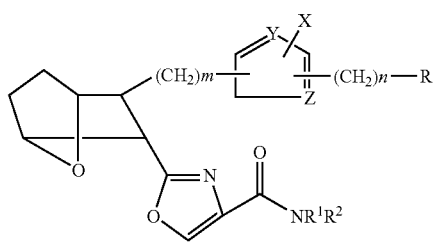

Preferably, $R^1$ and $R^2$ are selected from the group consisting of H, $C_1$-$C_6$ alkyl, $C_3$-$C_7$ cycloalkyl and $C_4$-$C_{12}$ alkylcycloalkyl.

Preferably $R^3$ and $R^4$ are selected from the group consisting of H, $C_1$-$C_6$ alkyl and hydroxyl derivatives thereof.

Preferably X is selected from the group consisting of hydrogen or halogen, e.g. fluoro.

The following Examples describe a method of synthesizing the prostamide antagonist compounds of the invention wherein the numbering of the Examples corresponds to the numbering of the various intermediates and final compounds shown in the reaction schemes, below.

Reaction Scheme 1.
Preparation of 2-bromo-4-fluoro-1-(methoxymethoxy)benzene 1

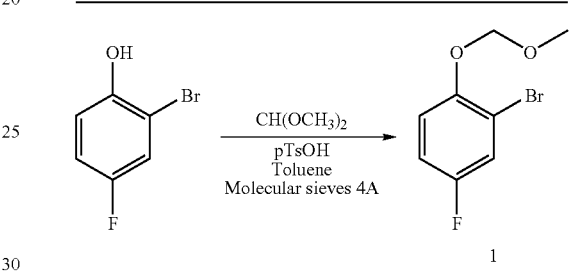

Reaction Scheme 2.
Preparation of phenol intermediate 9

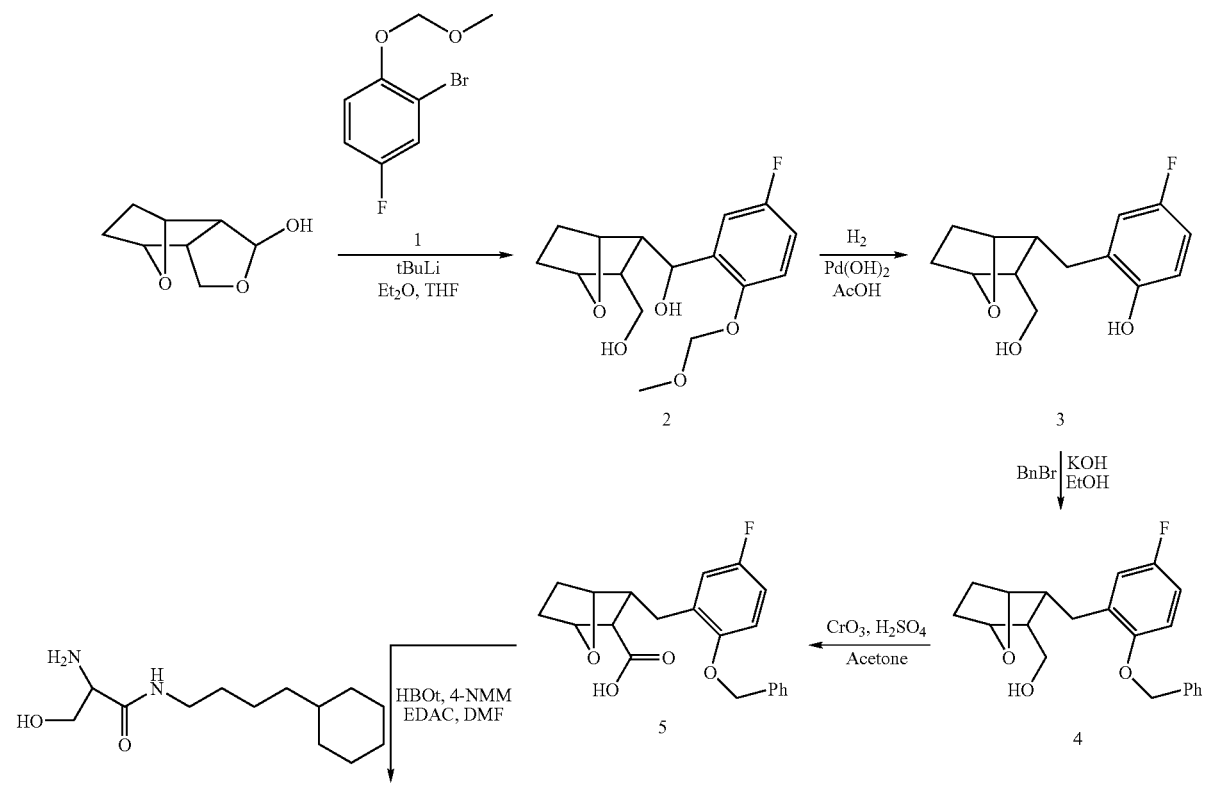

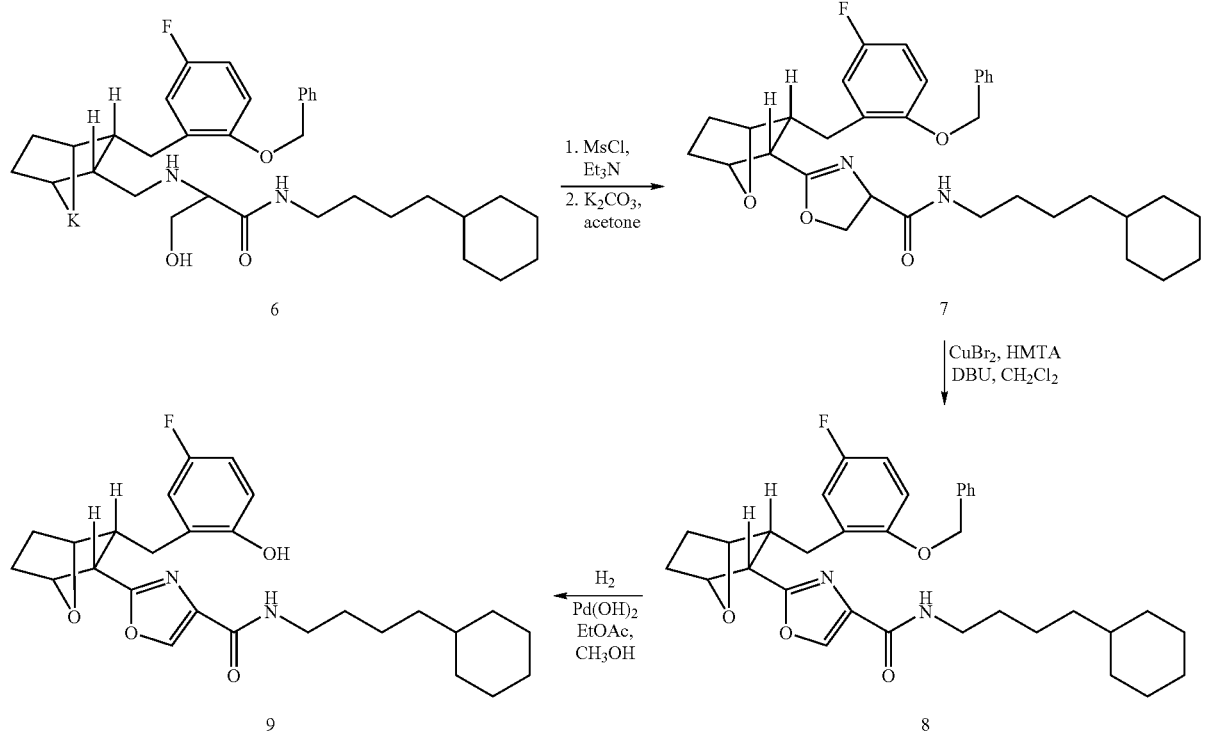

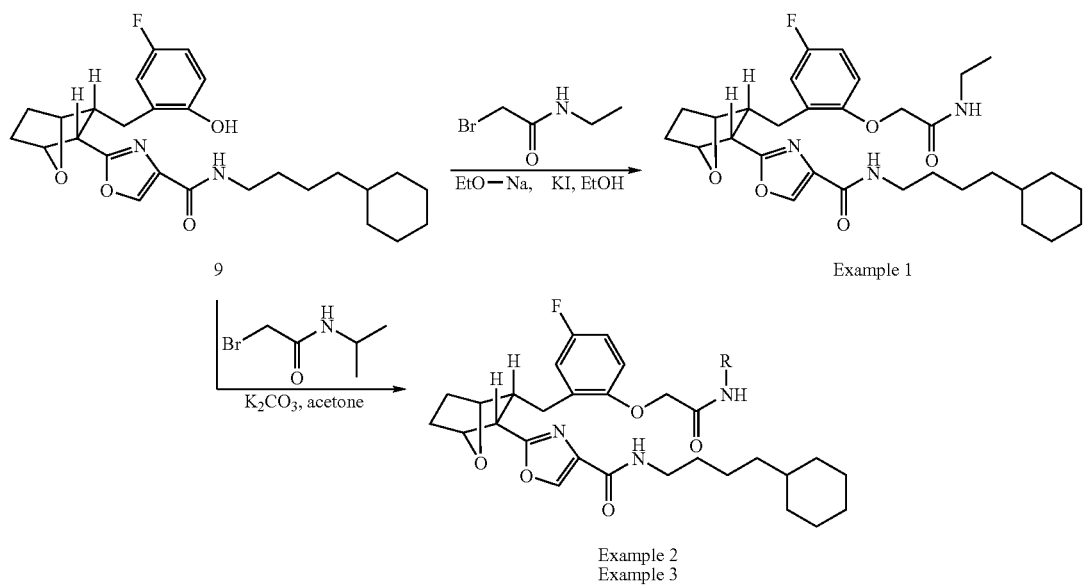

Reaction Scheme 3.
Preparation of prostamide antagonists of the Examples.

In carrying on the method of the invention as shown in Scheme 1, the protection reaction of 2-bromo-4-fluoro-1-(methoxymethoxy)benzene was carried out in the presence of an excess of dimethoxymethane and p-toluensulphonic acid to form the protected methoxymethyl phenol 1.

As shown in reaction scheme 2, the protected methoxymethyl phenol 1 in ethyl ether was treated with excess t-butyl-lithium to form the lithium salt that was reacted with the lactol shown (employing a molar ratio of 4:1) to prepare the alcohol 2.

The alcohol 2 (as a mixture of isomers) was subjected to a hydrogenation where in alcohol 2 is treated with hydrogen in the presence of $Pd(OH)_2/C$ and acetic acid to form the phenol 3.

Phenol 3 was treated with benzyl bromide and potassium hydroxide employing a molar ratio of 1.1:1 in ethanol. The mixture was heated at reflux to form the benzyl ether 4. The benzyl ether 4 was oxidized to the carboxylic acid 5 by treatment with Jones Reagent in the presence of acetone.

The carboxylic acid 5 was subjected to a coupling reaction wherein it was dissolved in DMF and N-(4-cyclohexylbutyl)-L-serine amide, 1-hydroxybenzotriazole hydrate, 4-methyl-morpholine and water soluble carbodiimide were added. The resulting mixture was stirred at room temperature for 16 h to form amide 6.

Amide 6 was mesylated by treating a solution of the amide in methylene chloride with an organic base such as triethylamine, pyridine or 2,6-lutidine and then while the mixture was held below 5° C., methanesulfonyl chloride was added to form the mesylate derivative. This was cyclized by dissolving it in acetone and heating in the presence of potassium carbonate to form the oxazoline 7.

Oxazoline 7 was oxidized using cupric bromide and 1,8-diazabicyclo[5.4.0]undec-7-ene (DBU) in the presence of hexamethylenetetramine and inert organic solvent such as methylene chloride to form oxazole 8.

The oxazole 8 was treated with hydrogen in the presence of Pd(OH)$_2$/C in a mixture of 2:1 ethyl acetate/methanol to form phenol 9.

As shown in reaction scheme 4, the phenol 9 intermediate was employed to prepare the prostamide antagonists EXAMPLE 1 and EXAMPLE 3.

The phenol 9 was treated with α-bromo-ethylacetamide in the presence of sodium ethoxide and potassium iodide to form ethyl amide EXAMPLE 1.

The phenol 9 was treated with α-bromopropylacetamide in the presence of potassium carbonate to form n-propyl amide EXAMPLE 2 and with α-bromoisopropylacetamide to form isopropyl amide EXAMPLE 3

EXAMPLE 1

[1S-(1α, 2α, 3α, 4α)]-2-[[3-[[(4-cyclohexylbutyl)-amino]-carbonyl]-2-oxazolyl]-7-oxabicyclo[2.2.1]hept-2-yl]methyl]-1-[[(ethylamino)-carbonyl]methoxy]-4-fluorobenzene.

Step 1

2-bromo-4-fluoro-1-(methoxymethoxy)benzene 1

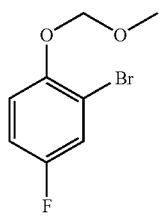

To a solution of 2-bromo-4-fluoro-phenol (1 g, 5.23 mmol) in CH$_2$Cl$_2$ (120 mL) was added p-toluenesulphonic acid (0.07 g, mmol), dimethoxymethane (2.31 mL, 26.15 mmol) and the resulting mixture was heated under reflux for 16 h under a soxhlett apparatus charged with freshly dried molecular 4 Å sieves. The reaction was allowed to warm to room temperature and washed with 2M sodium hydroxide (100 mL) then dried (Na$_2$SO4), filtered and the solvent was evaporated under vacuum to give title compound as an oil: 0.567 g, 46%.
$^1$H-NMR (CDCl$_3$, 300 MHz) δ7.31 (dd, 1H, J=2.9, 7.9 Hz, ArH), 7.13 (dd, 1H, J=4.9, 9.1 Hz, ArH), 6.98 (m, 1H, ArH), 5.21 (s, 2H, —OCH$_2$O—), 3.54 (s, 3H, —OCH$_3$)
$^{19}$F-NMR (CDCl$_3$, 300 MHz)-120.5

Step 2

[1S-(1α, 2α, 3α, (S*), 4α)]-α-[2-[methoxymethoxy]-4-fluoro-phenyl]-7-oxabicyclo[2.2.1]heptane-2,3-dimethanol

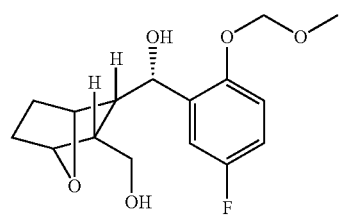

To a solution of 2-bromo-4-fluoro-1-(methoxymethoxy)benzene (1) (23.5 g, 100 mmol) in diethylether (250 mL), at −78° C. and under nitrogen atmosphere, was added drop wise a solution of t-butyllithium 1.7 M in pentane (100 mL, 170 mmol) and the resulting mixture was stirred for 45 minutes. Then, a solution of 4,10-dioxa-tricyclo[5.2.1.0*2,6*]decan-3-ol (6.24 g, 40 mmol) in THF (100 mL) was added and the reaction was left to warm to room temperature slowly and stirred for 16 h. After this time, the reaction was quenched by adding water (100 mL) and more diethyl ether (200 mL). The organic phase was extracted, washed with brine (100 mL), dried (MgSO$_4$), filtered and the solvent evaporated "under vacuum" to give the crude product as an oil. The crude product was purified by column chromatography using silica using a solvent gradient from ethyl acetate/hexane 2:1, 3:1 to 4:1 to isolate the title product as an oil: 8.1 g, 65%. $^1$H-NMR (CDCl$_3$, 300 MHz) δ 7.36 (dd, 1H, J=3.1, 9.5 Hz, ArH), 7.02 (dd, 1H, J=4.6, 9.1 Hz, ArH), 6.90 (dt, 1H, J=3.3, 8 Hz, ArH), 5.17 (s, 2H, —OCH$_2$O—), 5.14 (m, 1H, —CHOH), 4.66 (m, 2H, —CH—O—), 3.94 (m, 2H, —CH$_2$OH), 3.47 (s, 3H, —OCH$_3$), 2.39 (m, 1H, —CH—), 2.21 (m, 1H, —CH—), 1.74 (m, 2H, —CH$_2$—), 1.59 (m, 1H, —CH$_2$—), 1.35 (m, 1H, —CH$_2$—)

Step 3

[1S-(1α, 2α, 3α, 4α)]-2-[[3-[hydroxymethyl]-7-oxabicyclo[2.2.1]hept-2-yl]methyl]-4-fluoro-phenol

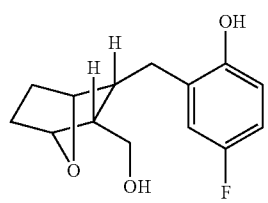

To a solution of [1S-(1α, 2α, 3α, (S*), 4α)]-α-[2-[methoxymethoxy]-4-fluoro-phenyl]-7-oxabicyclo[2.2.1]heptane-2,3-dimethanol (1.6 g, 5.12 mmol) in acetic acid (50 mL) was added palladium hydroxide (1.6 g, 2.28 mmol) and the resulting mixture was stirred under an atmosphere of hydrogen (Balloon) at room temperature for 24 h. The reaction mixture was filtered over Hyflo and the filtrate was concentrated under vacuum to give a crude oil. The crude product was purified by column chromatography on a 50G SPE cartridge using a solvent gradient from ethyl acetate/isohexane 1:2, 1:1 to 5:1 to isolate 0.71 g (55%) of title product as a white solid. $^1$H-NMR (CDCl$_3$, 300 MHz) δ 6.77 (m, 3H, ArH), 4.49 (m, 1H, —CH—O—), 4.31 (m, 1H, —CH—O—), 3.80 (m, 2H, —CH$_2$OH), 2.85 (m, 1H, —CH—), 2.55 (m, 1H, —CH—), 2.24 (m, 1H, —CH$_2$—), 2.12 (m, 1H, —CH$_2$—), 1.72 (m, 2H, —CH$_2$—), 1.42 (m, 2H, —CH$_2$—)

$^{19}$F-NMR (CDCl$_3$, 300 MHz)-124.6

Step 4

[1S-(1α, 2α, 3α, 4α)]-2-[[3-[hydroxymethyl]-7-oxabicyclo[2.2.1]hept-2-yl]methyl]-4-fluoro-1-phenylmethoxy-benzene

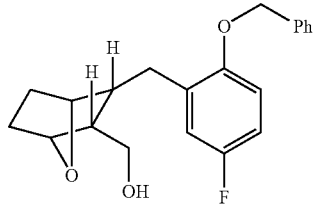

To a solution of [1S-(1α, 2α, 3α, 4α)]-2-[[3-[hydroxymethyl]-7-oxabicyclo[2.2.1]hept-2-yl]methyl]-4-fluoro-phenol (0.71 g, 2.8 mmol) in ethanol (30 mL) was added potassium hydroxide (0.173 g, 3.08 mmol) and the resulting mixture was refluxed until the potassium hydroxide dissolved. Then benzyl bromide (0.332 mL, 2.8 mmol) was added and the reaction was left to reflux for 16 h. After this time, the reaction was stopped and the solvent was evaporated under vacuum. The crude product was partitioned between ethyl acetate (30 mL) and 2M HCl (15 mL). The organic phase was separated; washed with a sat. solution of sodium bicarbonate (15 mL), brine (15 mL), dried (MgSO$_4$), filtered and the solvent was evaporated "under vacuum" to give the crude product as an oil. The crude product was purified by chromatography column on a 20G SPE cartridge using ethyl acetate/hexane 1:2 as eluent to isolate 0.906 g (94%) of titled product as an oil. $^1$H-NMR (CDCl$_3$, 300 MHz) δ 7.37(m, 5H, ArH), 6.86 (m, 3H, ArH), 5.08 (s, 2H, —OCH$_2$Ph), 4.56 (d, 1H, J=4.9 Hz, —CH—O—), 4.27 (d, 1H, J=4.9 Hz, —CH—O—), 3.74 (m, 2H, —CH$_2$OH), 2.86 (dd, 1H, J=4.4, 13.9 Hz, —CH—), 2.53 (dd, 1H, J=11.3, 13.7 Hz, —CH—), 2.29 (m, 1H, —CH$_2$—), 2.08 (m, 1H, —CH$_2$—), 1.80-1-32 (m, 4H, —CH$_2$—CH$_2$—)

Step 5

[1S-(1α, 2α, 3α, 4α)]-2-[[3-Carboxy-7-oxabicyclo[2.2.1]hept-2-yl]methyl]-4-fluoro-1-phenylmethoxy-benzene

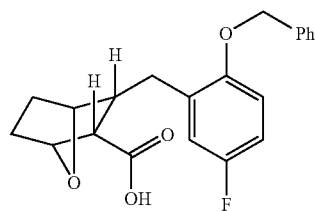

To a solution of [1S-(1α, 2α, 3α, 4α)]-2-[[3-[hydroxymethyl]-7-oxabicyclo[2.2.1]hept-2-yl]methyl]-4-fluoro-1-phenylmethoxy-benzene (0.812 g, 2.37 mmol) in acetone (20 mL) was added Jones reagent (1 mL) (The Jones reagent was prepared by dissolving 534 mg of Chromium oxide in 0.46 mL of acid sulphuric concentrated and 1.54 mL of water) and the resulting mixture was stirred for 10 min. Then, more Jones reagent (1 mL) was added and the mixture was stirred for 1 h. After, 2-propanol (0.6 mL) was added and the reaction was stirred for 5 min. Then the reaction was stopped, the chromium salts were filtered and the solvent was evaporated under vacuum. The crude product was partitioned between chloroform (30 mL) and 2 M HCl (15 mL). The organic phase was separated; it was washed with brine (15 mL), dried (Na$_2$SO$_4$), filtered and the solvent was evaporated "under vacuum" to give the titled compound as a dark solid which was used in the next step without any additional purification. $^1$H-NMR (CDCl$_3$, 300 MHz) δ 7.35 (m, 5H, ArH), 6.86 (m, 3H, ArH), 5.05 (s, 2H, —OCH$_2$Ph), 4.84 (bs, 1H, —CH—O—), 4.33 (bs, 1H, —CH—O—), 2.87 (m, 2H, —CH—), 2.57 (m, 2H, —CH$_2$—), 1.72 (m, 2H, —CH$_2$—CH$_2$—), 1.34 (m, 2H, —CH$_2$—CH$_2$—).

Step 6

[1S-(1α, 2α, 3α, (R*), 4α)]-2-[[3-[[[2-[(4-cyclohexylbutyl)-amino]-1-(hydroxymethyl)-2-oxoethyl]amino]carbonyl]-7-oxabicyclo[2.2.1]hept-2-yl]methyl]-4-fluoro-1-phenylmethoxy-benzene

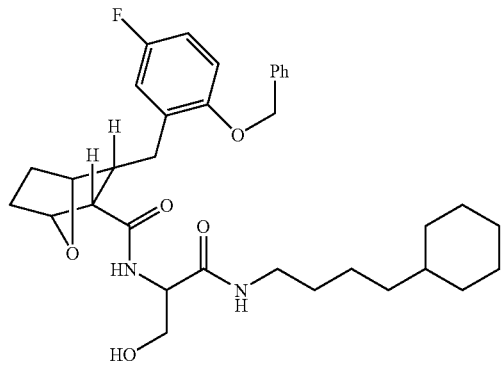

To a solution of [1S-(1α, 2α, 3α, 4α)]-2-[[3-Carboxy-7-oxabicyclo[2.2.1]hept-2-yl]methyl]-4-fluoro-1-phenylmethoxybenzene (0.3 g, 0.825 mmol), N-(4-cyclohexyl)butyl)-L-serinamide (0.2 g, 0.825 mmol), HBOt (0.122 g, 0.91 mmol), 4-methylmorpholine (0.1 mL, 0.91 mmol) in dimethylformamide (5 mL), at 0° C. and under nitrogen atmosphere, was added portion-wise EDAC (0.174 g, 0.91 mmol). The resulting mixture was stirred for 10 minutes then it was allowed to warm slowly to room temperature and stirred for 16 h. After this time, the reaction was stopped and the solvent was evaporated under vacuum. The crude material was partitioned between ethyl acetate (15 mL) and 2M HCl (10 mL). The organic phase was separated; it was washed with a sat. solution of sodium bicarbonate (10 mL), Brine (10 mL), dried (MgSO$_4$), filtered and the solvent evaporated "under vacuum" to give the titled product as an oil which was used in the next step without any additional purification. $^1$H-NMR (CDCl$_3$, 300 MHz) δ 7.30 (m, 5H, ArH), 7.03 (t, 1H, J=5.8 Hz, CONH), 6.80 (m, 4H, ArH+NH), 5.03 (s, 2H, —OCH$_2$Ph), 4.69 (d, 1H, J=5.1 Hz, —CH—O—), 4.42 (m, 1H, —CONHCHCO—), 4.33 (d, 1H, J=5.1 Hz, —CH—O—), 3.97 (dd, 1H, J=3.8, 11.3 Hz, —CH$_2$OH), 3.56 (dd, 1H, J=5.5, 11.3 Hz, —CH$_2$OH), 3.12 (m, 2H, —NCH$_2$—), 2.73-2.40 (m, 4H, —CH—+—CH$_2$—), 1.63-0.70 (m, 21H, —CH$_2$—CH$_2$—)

Step 7

[1S-(1α, 2α, 3α, 4α)]-2-[[3-[[(4-cyclohexylbutyl)-amino]-carbonyl]-4,5-dihydro-2-oxazolyl]-7-oxabicyclo[2.2.1]hept-2-yl]methyl]-4-fluoro-1-phenyl-methoxybenzene

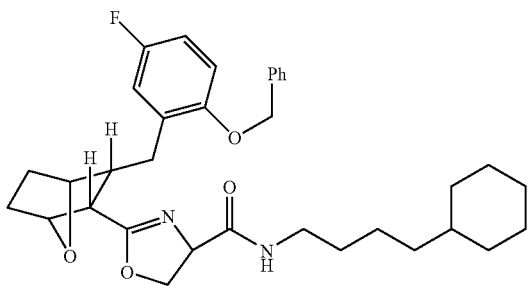

To a solution of [1S-(1α, 2α, 3α, (R*), 4α)]-2-[[3-[[[2-[(4-cyclohexylbutyl)-amino]-1-(hydroxymethyl)-2-oxoethyl]amino]carbonyl]-7-oxabicyclo[2.2.1]hept-2-yl]methyl]-4-fluoro-1-phenylmethoxy-benzene (1.54 g, 2.652 mmol) in dichloromethane (50 mL), at r.t. and under nitrogen atmosphere, was added triethylamine (0.923 mL, 6.63 mmol), mesyl chloride (0.256 mL, 3.315 mmol) and the resulting mixture was stirred for 1 h. The solvent was evaporated under vacuum and the crude product was dissolved in acetone (60 mL), potassium carbonate (1.47 g, 10.61 mmol) was added and the reaction was heated under reflux for 16 h. After this time, the solvent was evaporated under vacuum and the crude product was partioned between ethyl acetate (75 mL) and water (50 mL). The organic phase was separated; washed with brine (50 mL), dried (MgSO$_4$), filtered and the solvent evaporated "under vacuum" to give the title product as an oil which was used in the next step without any additional purification. $^1$H-NMR (CDCl$_3$, 300 MHz) δ 7.30 (m, 6H, ArH+NH), 6.84 (m, 3H, ArH), 6.55 (t, 1H, J=5.8 Hz, CONH), 5.08 (AB system, 2H, J=12.1 Hz, —OCH$_2$Ph), 4.83 (d, 1H, J=5.1 Hz, —CH—O—), 4.66 (dd, 1H, J=8.8, 10.6 Hz, —CONHCHCO—), 4.45 (m, 2H, —CH$_2$O—), 4.35 (d, 1H, J=5.1 Hz, —CH—O), 3.16 (m, 2H, —NCH$_2$—), 2.91 (d, 1H, J=8.6 Hz, —CH—), 2.72 (dd, 1H, J=2.9, 8.6 Hz, —CH—), 2.60-2.39 (m, 2H, —CH$_2$—), 1.63-0.70 (m, 21H, —CH$_2$—CH$_2$—).

Step 8

[1S-(1α, 2α, 3α, 4α)]-2-[[3-[[(4-cyclohexylbutyl)-amino]-carbonyl]-2-oxazolyl]-7-oxabicyclo[2.2.1]hept-2-yl]methyl]-4-fluoro-1-phenylmethoxybenzene

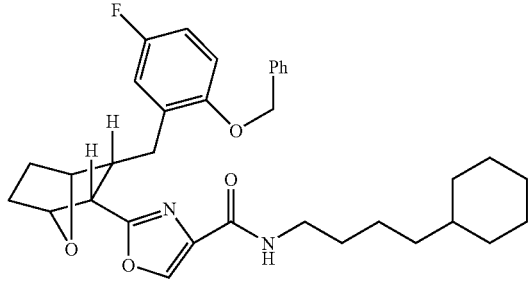

To a solution of copper bromide (2.37 g, 10.61 mmol) in dichloromethane (25 mL), at 0° C. and under a nitrogen atmosphere, were added HMTA (1.49 g, 10.61 mmol) and DBU (1.57 mL, 10.61 mmol) and the resulting mixture was stirred for 10 minutes. Next, a solution of [1S-(1α, 2α, 3α, 4α)]-2-[[3-[[(4-cyclohexylbutyl)-amino]-carbonyl]-4,5-dihydro-2-oxazolyl]-7-oxabicyclo[2.2.1]hept-2-yl]methyl]-4-fluoro-1-phenylmethoxybenzene (1.49 g, 2.652 mmol) in dichloromethane (15 mL) was added. And the reaction mixture was left to warm to room temperature slowly and stirred for 16 h. After this time, the solvent was evaporated under vacuum. The crude was partitioned between ethyl acetate (75 mL) and a 1:1 mixture of ammonium chloride/conc. ammonia (50 mL). The organic phase was separated; it was washed with a sat. solution of sodium bicarbonate (50 mL), brine (50 mL), dried (MgSO$_4$), filtered and the solvent was evaporated "under vacuum" to give the crude as an oil. The crude product was purified by column chromatography on a 50G SPE cartridge using a solvent gradient from ethyl acetate/iso-hexane 2:1; 5:1; to only ethyl acetate to isolate 0.595 g (56%) of the title compound as an oil. $^1$H-NMR (CDCl$_3$, 300 MHz) δ 8.08 (s, 1H, =CH—O—), 7.38 (m, 6H, ArH+NH), 6.93 (t, 1H, J=5.8 Hz, CONH), 6.81 (m, 3H, ArH), 5.05 (s, 2H, —OCH$_2$Ph), 4.95 (d, 1H, J=5.1 Hz, —CH—O—), 4.42 (d, 1H, J=5.1 Hz, —CH—O), 3.35 (m, 3H, —NCH$_2$—+—CH—), 2.67 (m, 1H, —CH—), 2.32 (m, 2H, —CH$_2$—), 1.87-0.84 (m, 21H, —CH$_2$—CH$_2$—).

Step 9

[1S-(1α, 2α, 3α, 4α)]-2-[[3-[[(4-cyclohexylbutyl)-amino]-carbonyl]-2-oxazolyl]-7-oxabicyclo[2.2.1]hept-2-yl]methyl]-4-fluoro-phenol

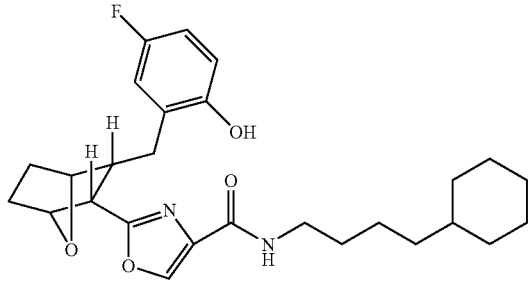

To a solution of [1S-(1α, 2α, 3α, 4α)]-2-[[3-[[(4-cyclohexylbutyl)-amino]-carbonyl]-2-oxazolyl]-7-oxabicyclo

[2.2.1]hept-2-yl]methyl]-4-fluoro-1-phenylmethoxybenzene (0.85 g, 1.51 mmol) in a mixture of ethyl acetate/methanol 2:1 (135 mL) was added palladium hydroxide (0.85 g, 1.2 mmol) and the resulting mixture was stirred under an atmosphere of hydrogen (balloon) at room temperature for 24 h. The reaction mixture was filtered over Hyflo and the filtrate was concentrated under vacuum to give the title compound as oil that was used in the next step without any additional purification ¹H-NMR (CDCl₃, 300 MHz) δ 8.25 (s, 1H, =CH—O—), 7.05 (t, 1H, J=5.8 Hz, CONH), 6.76 (m, 4H, ArH+NH), 5.02 (d, 1H, J=5.1 Hz, —CH—O—), 4.43 (d, 1H, J=5.1 Hz, —CH—O), 3.40 (m, 3H, —NCH₂—+—CH—), 2.66 (m, 1H, —CH—), 2.20 (m, 2H, —CH₂—), 1.88-0.85 (m, 21H, —CH₂—CH₂—)

Step 10

[1S-(1α, 2α, 3α, 4α)]-2-[[3-[[(4-cyclohexylbutyl)-amino]-carbonyl]-2-oxazolyl]-7-oxabicyclo[2.2.1]hept-2-yl]methyl]-1-[[(ethylamino)-carbonyl]methoxy]-4-fluorobenzene.

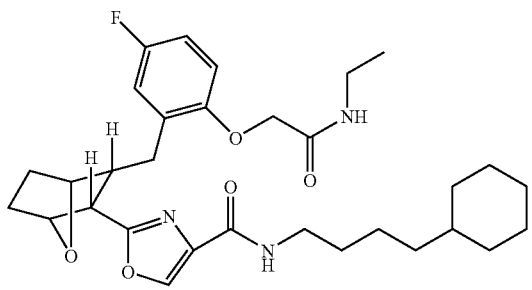

A small crop of sodium was dissolved in ethanol (3 mL). To this solution was added a solution of [1S-(1α, 2α, 3α, 4α)]-2-[[3-[[(4-cyclohexylbutyl)-amino]-carbonyl]-2-oxazolyl]-7-oxabicyclo[2.2.1]hept-2-yl]methyl]-4-fluoro-phenol (0.045 g, 0.1 mmol) in a mixture 1:1 of ethanol and methylene chloride (4 mL) and the resulting mixture was stirred at room temperature for 30 minutes. Then α-bromo-ethylacetamide (0.025 g, 0.15 mmol) and potassium iodide (0.001 g, 0.01. mmol) were added and the resulting mixture was heated under reflux for 16 h. After this time the solvent was evaporated under vacuum and the crude mixture was partitioned between ethyl acetate (20 mL) and water (10 mL). The organic phase was separated and washed with 2M sodium hydroxide (10 mL), brine (10 mL), dried (MgSO₄), filtered and the solvent was evaporated "under vacuum" to give the crude product as an oil. The crude material was purified by column chromatography on a 10G SPE cartridge using a gradient of ethyl acetate/hexane from 1:3; 1:1; 2:1; to neat ethyl acetate to isolate 0.010 g (18%) of the title compound as a white solid ¹H-NMR (CDCl₃, 300 MHz) δ 8.14 (s, 1H, =CH—O—), 7.42 (m 1H, CONH), 6.87 (m, 4H, ArH+NH), 5.04 (d, 1H, J=5.1 Hz, —CH—O—), 4.51 (AB system, 1H, J=13.9 Hz, —O—CH₂—CONH—), 4.29 (m, 1H, —CH—O—), 4.32 (AB system, 1H, J=13.9 Hz, —O—CH₂—CONH—), 3.40 (m, 5H, 2×—NCH₂—+—CH—), 2.58 (m, 2H, —CH—+—CH₂—), 1.94 (m, 1H, —CH₂—), 1.88-0.85 (m, 24H, —CH₂—CH₂— and —CONHCH2CH₃) ¹⁹F-NMR (CDCl₃, 300 MHz) δ 122.4.

EXAMPLE 2

[1S-(1α, 2α, 3α, 4α)]-2-[[3-[[(4-cyclohexylbutyl)-amino]-carbonyl]-2-oxazolyl]-7-oxabicyclo[2.2.1]hept-2-yl]methyl]-1-[[(ethylamino)-carbonyl]methoxy]-4-fluorobenzene.

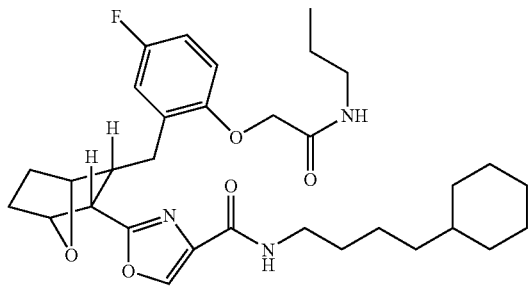

To a solution of [1S-(1α, 2α, 3α, 4α)]-2-[[3-[[(4-cyclohexylbutyl)-amino]-carbonyl]-2-oxazolyl]-7-oxabicyclo[2.2.1]hept-2-yl]methyl]-4-fluoro-phenol (example 1 step 9) (0.941 g, 2 mmol) in acetone (20 mL) was added α-bromopropylacetamide (0.6 g, 3.9 mmol), potassium carbonate (0.304 g, 2.2. mmol) and the resulting mixture was heated at 65° C. for 16 h. After this time, the solvent was evaporated under vacuum to give the crude product as a thick gum. The crude product was purified by column chromatography on a 20G SPE cartridge using methylene chloride/methanol 10% as eluent to isolate 0.045 g (4%) of the title compound as a white solid. ¹H-NMR (CDCl₃, 300 MHz) δ 8.13 (s, 1H, =CH—O—), 7.38 (m 1H, CONH), 6.81 (m, 4H, ArH+NH), 5.03 (d, 1H, J=5.1 Hz, —CH—O—), 4.55 (AB system, 1H, J=13.9 Hz, —O—CH₂—CONH—), 4.34 (m, 2H, —CH—O—), 4.33 (AB system, 1H, J=13.9 Hz, —O—CH₂—CONH—), 3.35 (m, 5H, 2×—NCH₂—+—CH—), 2.50 (m, 2H, —CH—+—CH₂—), 1.95 (m, 1H, —CH₂—), 1.88-0.85 (m, 26H, —CH₂—CH₂— and —CONHCH₂CH₂CH₃) ¹⁹F-NMR (CDCl₃, 300 MHz) δ122.4.

EXAMPLE 3

[1S-(1α, 2α, 3α, 4α)]-2-[[3-[[(4-cyclohexylbutyl)-amino]-carbonyl]-2-oxazolyl]-7-oxabicyclo[2.2.1]hept-2-yl]methyl]-1-[[(ethylamino)-carbonyl]methoxy]-4-fluorobenzene.

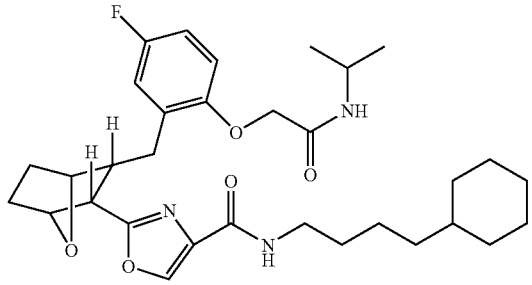

To a solution of [1S-(1α, 2α, 3α, 4α)]-2-[[3-[[(4-cyclohexylbutyl)-amino]-carbonyl]-2-oxazolyl]-7-oxabicyclo[2.2.1]hept-2-yl]methyl]-4-fluoro-phenol (example 1 step 9) (0.941 g, 2 mmol) in acetone (20 mL) was added α-bromoisopropylacetamide (0.610 g, 3.39 mmol), potassium carbonate (0.304 g, 2.2. mmol) and the resulting mixture was heated at 65° C. for 16 h. After this time, the solvent was evaporated under vacuum to give the crude product as a thick gum. The crude product was purified by column chromatography on a 20G SPE cartridge using methylene chloride/methanol 10% as eluent to isolate 0.038 g (3%) of the title compound as a white solid. $^1$H-NMR (CDCl$_3$, 300 MHz) δ 8.14 (s, 1H, =CH—O—), 7.25 (m 1H, CONH), 6.81 (m, 4H, ArH+NH), 5.06 (d, 1H, J=5.1 Hz, —CH—O—), 4.51 (AB system, 1H, J=13.9 Hz, —O—CH$_2$—CONH—), 4.29 (m, 2H, —CH—O— and —CONHCH(CH$_3$)$_2$), 4.27 (AB system, 1H, J=13.9 Hz, —O—CH$_2$—CONH—), 3.40 (m, 3H, —NCH$_2$—+—CH—), 2.52 (m, 2H, —CH—+—CH$_2$—), 1.92 (m, 1H, —CH$_2$—), 1.88-0.85 (m, 27H, —CH$_2$—CH$_2$— and —CONHCH(CH$_3$)$_2$) $^{19}$F-NMR (CDCl$_3$, 300 MHz) δ122.5.

LC-MS: m/z 570 M+H$^+$

Methods

Test Systems Used

The test systems employed included the isolated feline iris as a key preparation since both prostamides (prostaglandin ethanolamides) and prostanoid FP receptor agonists potently elicit a contractile response in this tissue (Woodward et al., 2003; Matias et al., 2004). Activity at human prostanoid receptors was determined using recombinant receptors stably transfected into HEK-293 EBNA cells, using chimeric G proteins to enable Ca$^{2+}$ signal responses to all receptor subtypes, as previously described (Woodward et al., 2003: Matias et al, 2004)

Measurements (1) Feline Iris

Claas A laboratory bred cats were housed communally in USDA and AAALAC approved facilities, with standards that exceeded those for enrichment and group housing. Water was available ad libitum and food was standard cat nutritional diet. They were kept on a 12 hr light-dark cycle. They (96) were euthanized by i.v. overdose of sodium pentobarbital (Anthony, Arcadia, Calif.). The eyes were enucleated immediately thereafter and placed on ice. Two eyes provided a total of four iridial preparations. The iris sphincter was mounted vertically under 50- to 100 mg tension in a jacketed 10 ml organ bath. Smooth muscle tension of the isolated iris sphincter was measured isometrically with force displacement transducers (Grass FT-03) and recorded on a Grass polygraph (Model 7). The organ baths contained Krebs' solution maintained at 37° C. by a heat exchanger and circulating pump. The Krebs' solution was gassed with 95% O$_2$, 5% CO$_2$ to give a pH of 7.4. and had the following composition: 118.0 mM NaCl, 4.7 mM KCl, 1.2 mM KH$_2$PO$_4$, 1.9 mM CaCl$_2$, 1.18 mM MgSO$_4$, 25.0 mM NaHCO$_3$, 11.7 mM glucose and 0.001 mM indomethacin. A 60 min stabilization period was provided before commencing each experiment. Activity was manifest as contractile responses and measured as such. These investigations were humane as possible and adhered to the "ARVO resolution on the Use of Animals in Research".

(2) Ca$^{2+}$ Signal Studies on Human Recombinant Prostanoid Receptors

The use of chimeric G protein cDNAs allowed responses to G$_s$ and G$_i$ coupled prostanoid receptors to be measured as a Ca$^{2+}$ signal, as previously described (Woodward et al., 2003; Matias et al., 2004). Prostanoid DP, EP$_2$, and EP$_4$ receptor cDNAs were co-transfected with chimeric G$_{qs}$ cDNA containing a haemagglutanin (HA) epitope. The prostanoid EP$_3$ receptor was co-transfected into HEK-293 EBNA cells, using pCEP$_4$ as a vector, with chimeric G$_{qi}$-HA. G$_{qs}$ and G$_{qi}$ chimeric cDNAs (Molecular Devices, Sunnyvale, Calif.) were cloned into a pCEP$_4$ vector and also selected by using a hygromycin B selection marker. Transfection into HEK-293 EBNA cells was achieved by the FuGENE 6 method. Because G$_{qs}$ and G$_{qi}$ contained an HA epitope, protein expression was detected by Western blotting analysis using anti-mouse HA monoclonal antibody and HRP conjugated secondary antibody. For human recombinant EP$_1$, FP, IP, and TP receptors, stable transfectants were obtained as previously described (Woodward et al., 2003; Matias et al., 2004). Briefly, pCEP$_4$ was used as the expression vector and transfection into HEK-293-EBNA cells was performed with FuGENE 6. Stable transfectants were again selected according to hygromycin resistance.

Ca$^{2+}$ signaling studies were performed using a FLIPR (fluorometric imaging plate reader) instrument. Cells were seeded at a density of 5×10$^4$ cells/well in Biocoat poly-D-lysine coated, black wall, clear bottom 96 well plates (BD Biosciences, Franklin Lakes, N.J.) and allowed to attach overnight in an incubator at 37° C. The cells were then washed twice with HBSS-HEPES buffer (Hanks' balanced salt solution without bicarbonate and phenol red, 20 mM HEPES, pH 7.4) using a Denley Cellwash plate washer (Labsystems, Franklin, Mass.). After 45-60 min of dye-loading in the dark using the Ca$^{2+}$-sensitive dye Fluo-4AM, at a final concentration of 2×10$^{-6}$M, the plates were washed 4 times with HBSS-HEPES buffer to remove excess dye and leaving 100 µl of buffer in each well. The plates were then placed in the FLIPR instrument and allowed to equilibrate at 37° C. Compound solutions were added in a 50 µl volume to each well to give the desired final concentration. Cells were excited with an argon laser at 488 nm and emission was measured through a 510-570 nm band width emission filter (FLIPR, Molecular Devices, Sunnyvale, Calif.). The peak increase in fluorescence intensity was recorded for each well.

Experimental Design

The feline iris experiments were designed so that a direct, four-way comparison for antagonist vs. prostamide, vehicle vs. prostamide, antagonist vs. corresponding PG, and vehicle vs. corresponding PG was provided in tissue preparations obtained from a single animal. One cumulative dose-response curve to agonist was obtained in each tissue. Vehicle (ethanol) and antagonist (AGN 204396) were given 30 minutes before the agonist dose-response curves were constructed. The response to PGF$_{2\alpha}$10$^{-7}$M was determined at the beginning and end of each dose response curve, with appropriate wash-out, and responses were calculated as % of this reference contraction.

The experimental design for the FLIPR studies was as follows. On each plate, four wells each served as negative (HBSS-HEPES buffer) and positive controls (standard agonist: DP=BW 245C, EP$_1$-EP$_4$=PGE$_2$, FP=PGF$_{2\alpha}$, IP=carbaprostacyclin TP=U-46619). The peak fluorescence change in each well containing drug was expressed relative to the controls. To obtain concentration-response curves, compounds were tested in duplicate in each plate over the desired concentration range. Each compound was tested on at least 3 separate plates using cells from different passages to give n=3. The results are reported in Table 1, below.

TABLE 1

| COMPOUND # | STRUCTURE R | $K_b$ (nM) Pamide | FP | DP | $EP_1$ | $EP_2$ | $EP_3$ | $EP_4$ | IP | TP |
|---|---|---|---|---|---|---|---|---|---|---|
| | | Cat Iris | Cat Iris (h FP) | h | h | h | h | h | h | h |
| AGN 211334 | | 236 | NA(NA) | NA | NA | NA | NA | 37,048 | NA | 16 |
| AGN 211335 | | 356 | 54,000 (33,600) | NA | NA | NA | NA | 9046 | NA | 100 |
| AGN 211336 | | 303 | NA (13,136) | 40861 | NA | NA | NA | NA | NA | 111 |

(NA = inactive)

Surprisingly, the compounds of this invention are more potent than the compounds of U.S. Pat. No. 7,045,634.

The prostamide antagonists of the present invention may be used to test for compounds having prostamide receptor agonist activity and not activity at the corresponding prostaglandin receptor as follows:

A tissue or cell responsive to a prostaglandin and a prostamide, e.g. cat iris sphincter tissue, is contacted with various concentrations of said prostaglandin and a first response is measured in a concentration dependent manner. (Preferably, the cat iris sphincter tissue may be dissected into four paired preparations for the purpose of the following test.) Said tissue or cell is contacted with said various concentrations of said prostaglandin in the presence of a prostamide antagonist and a second response is measured in a concentration dependent manner.

Said tissue or cell is contacted with various concentrations of a compound which is to be evaluated for prostamide agonist activity and a third response is measured in a concentration dependent manner. Said tissue or cell is contacted with said various concentrations of said compound which is to be evaluated for prostamide agonist activity in the presence of said prostamide antagonist and a fourth response is measured in a concentration dependent manner.

Compounds having prostamide agonist activity are determined as compounds wherein the difference between said third and fourth response is greater than the difference between said first and second response.

Preferably, the difference between said first and second response is substantially negligible, i.e. the prostaglandin has substantially no prostamide agonist activity, therefore the presence of the prostamide antagonist does not affect the tissue response. Thus, prostamide agonists are compounds wherein the response in the presence of the prostamide antagonist is negligible as compared to the response in the absence of the prostamide antagonist.

In another aspect of the present invention, the relative activity of a prostamide agonist may be measured by contacting two or more prostamide agonists with a tissue or cell that is responsive to a prostamide agonist in the presence of a specified concentration of a prostamide antagonist of this invention. The relative activity of each of said prostamide agonists is determined by comparing the relative response of said tissue or cell.

The compounds of the invention can be administered orally, parenterally, or topically to various mammalian species known to be subject to hyperpigmentary disorders of the skin, hair, internal organs or other pigmented cells or excessive hair growth, e.g., humans, cats, dogs and the like in an effective amount within the dosage range of about 0.1 to about 100 mg/kg, preferably about 0.2 to about 50 mg/kg and more preferably about 0.5 to about 0.5 to about 25 mg/kg (or from about 1 to about 2500 mg, preferably from about 5 to about 2000 mg) on a regimen in single or 2 to 4 divided daily doses. For inflammatory disorders, the compounds of the invention may be give topically, orally, or by local injection as above.

The active ingredient can be utilized in a composition such as tablet, capsule, solution or suspension containing about 5 to about 500 mg per unit of dosage of a compound or mixture of compounds of formulas I, II or III in topical form for reducing pigmentation or hair growth, etc. (0.01 to 5% by weight compound of formulas I, II or III, 1 to 5 treatments per day). They may be compounded in conventional matter with a physiologically acceptable vehicle or carrier, excipient, binder, preservative, stabilizer, flavor, etc., or with a topical carrier such as mineral oil as called for by accepted pharmaceutical practice.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds. Different pharmaceutical compositions, including the prostamide antagonists of this invention, may be prepared and used with substantially the same result. Finally, while the above invention has been described with reference to the compound of formulas I, II or III, above, the compounds described below may be included within the scope of this invention:

[1S-(1α,2α,3α,4α)]-2-[[3-[[4-[(cycloalkyl polymethylenyl)-amino]-carbonyl]-2-heteroaryl-7-oxabicyclo [2.2.1] hept-2-yl]-1-[[(hydrocarbylamino)-carbonyl] methoxy aryl, wherein "Cycloalkyl" refers to a cyclic saturated aliphatic hydrocarbon group. Preferably, the cycloalkyl group has 3 to 12 carbons. More preferably, it has from 3 to 7 carbons, most preferably 5 or 6 carbons.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of $C_1$-$C_6$ alkyl, hydroxyl, halogen, $COOR^6$, $NO_2$, $CF_3$, $N(R^6)_2$, $CON(R^6)_2$, $SR^6$, sulfoxy, sulfone, CN and $OR^6$, wherein $R^6$ is $C_1$-$C_6$ alkyl. Preferably, the aryl group has 6 to 20 carbons. More preferably, it has from 6 to 10 carbons, most preferably 6 carbons.

"Heteroaryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like. Preferably, the heteroaryl group has from 2 to 10 carbons. More preferably, it has from 3 to 10 carbons, most preferably 3 carbons.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Polymethylenyl" refers to a radical having the structure —$(CH_2)_n$— wherein n is an integer of from 2 to 10, preferably from 2 to 6, e.g. 4 or 5.

Thus, however detailed the foregoing may appear in text, it should not be construed as limiting the overall scope hereof, rather, the ambit of the present invention is to be governed only by the lawful construction of the appended claims.

The invention claimed is:

1. A compound having prostamide receptor antagonist activity represented by the general formula I:

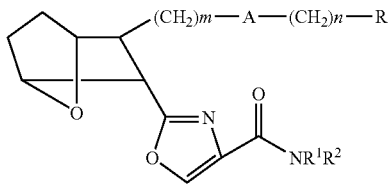

wherein m is an integer of from 1 to 3;

A is an aryl or heteroaryl radical having from 6 to 14 carbon atoms, wherein said heteroaryl may be substituted with one or more oxygen, sulfur or nitrogen in the heteroaryl ring and heteroatom substituted derivatives thereof;

n is 0 or an integer of from 1 to 4;

R is $OCH_2CONR^3R^4$;

$R^1$ and $R^2$ are independently selected from the group consisting of H, $C_1$-$C_6$ alkyl, $C_2$-$C_6$ alkenyl, $C_2$-$C_6$ alkynyl, $C_3$-$C_7$ cycloalkyl, $C_4$-$C_{12}$ alkylcycloalkyl, $C_6$-$C_{10}$ aryl, $C_7$-$C_{12}$ alkyl aryl radicals and heteroatom-substituted derivatives thereof, wherein one or more of the hydrogen or carbon atoms in said radicals is replaced with a halogen, oxygen, nitrogen or sulfur-containing radical;

$R^3$ and $R^4$ are selected from the group consisting of H, $C_1$-$C_6$ alkyl, $C_2$-$C_6$ alkenyl, $C_2$-$C_6$ alkynyl, $C_3$-$C_7$ cycloalkyl, $C_4$-$C_{12}$ alkylcycloalkyl, $C_6$-$C_{10}$ aryl, $C_7$-$C_{12}$ alkyl aryl radicals and heteroatom-substituted derivatives thereof, wherein one or more of the hydrogen or carbon atoms in said radicals is replaced with a halogen, oxygen, nitrogen or sulfur-containing radical and pharmaceutically acceptable salts thereof.

2. The compounds of claim 1 represented by formula II

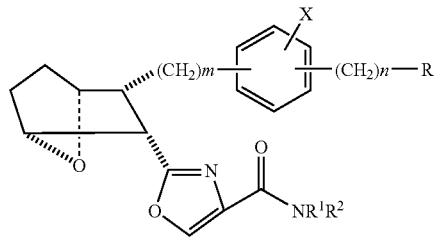

wherein X is selected from the group consisting of H, $C_1$-$C_6$ alkyl, hydroxyl, halogen, $COOR^6$, $NO_2$, $CF_3$, $N(R^6)_2$, $CON(R^6)_2$, $SR^6$, sulfoxy, sulfone, CN and $OR^6$, wherein $R^6$ is $C_1$-$C_6$ alkyl.

3. The compounds of claim 2 wherein m is 1 or 2.

4. The compounds of claim 2 wherein n is from 2 to 4.

5. The compounds of claim 2 wherein $R^1$ and $R^2$ are selected from the group consisting of H, $C_1$-$C_6$ alkyl, $C_3$-$C_7$ cycloalkyl and $C_4$-$C_{12}$ alkylcycloalkyl.

6. The compounds of claim 2 wherein X is hydrogen or halogen.

7. The compounds of claim 6 wherein X is fluoro.

8. The compounds of claim 1 represented by formula III

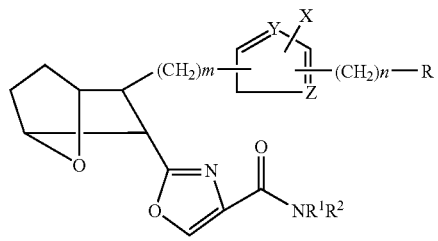

wherein Y is O or S, Z is N or CH and wherein X is selected from the group consisting of H, $C_1$-$C_6$ alkyl, hydroxyl, halogen, $COOR^6$, $NO_2$, $N(R^6)_2$, $CON(R^6)_2$, $SR^6$, sulfoxy, sulfone, CN and $OR^6$, wherein $R^6$ is $C_1$-$C_6$ alkyl.

9. The compound of claim 8 wherein m is 1 or 2.

10. The compound of claim 8 wherein n is 2 to 4.

11. The compound of claim 8 wherein $R^1$ and $R^2$ are selected from the group consisting of H, $C_1$-$C_6$ alkyl, $C_3$-$C_7$ cycloalkyl and $C_4$-$C_{12}$ alkylcycloalkyl.

12. The compound of claim 8 wherein X is hydrogen or halogen.

13. The compound of claim 12 wherein X is fluoro.

14. The compound of claim 1 wherein the compound is [1S-(1α, 2α, 3α, 4α)]-2-[[3-[[(4-cyclohexylbutyl)-amino]-carbonyl]-2-oxazolyl]-7-oxabicyclo[2.2.1]hept-2-yl]methyl]-1-[[(ethylamino)-carbonyl]methoxy]-4-fluorobenzene.

15. The compound of claim 1 wherein the compound is [1S-(1α, 2α, 3α, 4α)]-2-[[3-[[(4-cyclohexylbutyl)-amino]-carbonyl]-2-oxazolyl]-7-oxabicyclo[2.2.1]hept-2-yl]methyl]-1-[[(2-propyl-amino)-carbonyl]methoxy]-4-fluorobenzene.

16. The compound of claim 1 wherein the compound is [1S-(1α, 2α, 3α, 4α)]-2-[[3-[[(4-cyclohexylbutyl)-amino]-carbonyl]-2-oxazolyl]-7-oxabicyclo[2.2.1]hept-2-yl]methyl]-1-[[(2-methylethylamino)-carbonyl]methoxy]-4-fluorobenzene.

17. A method of testing for compounds having prostamide receptor agonist activity and not activity at the corresponding prostaglandin receptor which comprises;
contacting a tissue or cell responsive to a prostaglandin and a prostamide with various concentrations of said prostaglandin and measuring a first response in a concentration dependent manner contacting said tissue or cell with said various concentrations of said prostaglandin in the presence of a prostamide antagonist according to claim 1 and measuring a second response in a concentrated dependent manner,
contacting said tissue or cell with various concentrations of a compound which is to be evaluated for prostamide agonist activity and measuring a third response in a concentration dependent manner,
contacting said tissue or cell with said various concentrations of said compound which is to be evaluated for prostamide agonist activity in the presence of said prostamide antagonist and measuring a fourth response in a concentration dependent manner, and determining compounds having prostamide agonist activity as compounds wherein the difference between said third and fourth response is greater than the difference between said first and second response.

18. The method of claim 17 wherein said tissue is cat iris sphincter tissue.

19. The method of claim 17 wherein said tissue is cat lung tissue.

20. The method of claim 17 wherein said tissue is rabbit uterine tissue.

21. A method of measuring the relative activity of a prostamide agonist by contacting two or more prostamide agonists with a tissue that is responsive to a prostamide agonist in the presence of a specified concentration of a prostamide antagonist according to claim 1 and determining the relative activity of each of said prostamide agonists by comparing the relative response of said tissue.

22. A compound having prostamide receptor antagonist activity that is [1S-(1α,2α,3α,4α)]-2-[[3-[[(4-cycloalkyl polymethylenyl)-amino]-carbonyl]-2-heteroaryl-7-oxabicyclo [2.2.1]hept-2-yl]1-[[hydrocarbylamino)-carbonyl]methoxy aryl, wherein said cycloalkyl is a cyclic saturated aliphatic hydrocarbon group;
aryl is an aromatic group which has at least one ring having a conjugated pi electron system and is selected from the group consisting of carbocyclic aryl, heterocyclic aryl and biaryl groups, wherein the aryl group may be optionally substituted with one or more substituents selected from the group consisting of $C_1$-$C_6$ alkyl, hydroxyl, halogen, $COOR^6$, $NO_2$, $CF_3$, $N(R^6)_2$, $CON(R^6)_2$, $SR^6$, sulfoxy, sulfone, CN and $OR^6$, wherein $R^6$ is $C_1$-$C_6$ alkyl; heteroaryl is an aryl group having from 1 to 3 heteroatoms as ring atoms, the remainder of the ring atoms being carbon and said heteroatoms are selected from the group consisting of oxygen, sulfur and nitrogen and hydrocarbyl is a hydrocarbon group having only carbon and hydrogen atoms.

23. The compound of claim 22 wherein said heteroaryl is selected from the group consisting of furanyl, thienyl, pyridyl, pyrrolyl, N-lower alkyl pyrrolo, pyrimidyl, pyrazinyl and imidazolyl.

24. The compound of claim 22 wherein said hydrocarbyl has from 1 to 20 carbon atoms.

25. The compound of claim 22 wherein said cycloalkyl has from 3 to 12 carbon atoms, said heteroaryl has from 2 to 10 carbon atoms and said aryl has from 6 to 20 carbon atoms.

26. A compound selected from the group consisting of

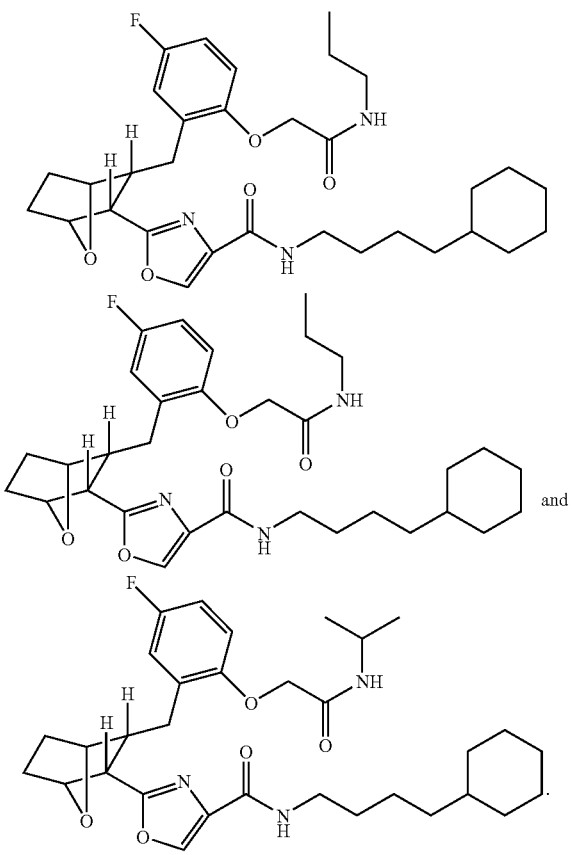

27. A compound that is [1S-(1α,2α,3α,4α)]-2-[[3-[[(4-cycloalkyl polymethylenyl)-amino]-carbonyl]-2-heteroaryl-7-oxabicyclo [2.2.1]hept-2-yl]-1-[[hydrocarbylamino)-carbonyl]methoxy aryl.

* * * * *